United States Patent [19]

Schlecker et al.

[11] Patent Number: 5,631,261
[45] Date of Patent: May 20, 1997

[54] TRIAZOLOQUINAZOLINES, THEIR PREPARATION AND USE

[75] Inventors: Rainer Schlecker, Bissersheim; Hans-Joerg Treiber, Bruehl; Berthold Behl, Ludwigshafen; Hans P. Hofmann, Limburgerhof, all of Germany

[73] Assignee: BASF Aktiengesellschaft, Ludwigshafen, Germany

[21] Appl. No.: 446,844

[22] PCT Filed: Nov. 27, 1993

[86] PCT No.: PCT/EP93/03331

§ 371 Date: Jun. 1, 1995

§ 102(e) Date: Jun. 1, 1995

[87] PCT Pub. No.: WO94/13672

PCT Pub. Date: Jun. 23, 1994

[30] Foreign Application Priority Data

Dec. 10, 1992 [DE] Germany .................... 42 41 563.2

[51] Int. Cl.⁶ .................... C07D 487/04; A61K 31/495
[52] U.S. Cl. .................... 514/267; 544/247; 544/251; 514/257
[58] Field of Search ................. 514/267, 257; 544/251, 247

[56] References Cited

U.S. PATENT DOCUMENTS 4,053,600  10/1977  Hardtmann et al. .............. 544/119
4,128,644  12/1978  Vogt .............................. 544/250
4,463,007  7/1984   Schlecker et al. .............. 544/251
5,153,196  10/1992  McQuaid et al. ................. 544/250

FOREIGN PATENT DOCUMENTS 80176  6/1983  European Pat. Off. .

OTHER PUBLICATIONS

J. Med. Chem. (1991), 34, 281–290, Francis et al., Synthesis and Benzodiazepine Binding . . . .

Primary Examiner—John M. Ford
Attorney, Agent, or Firm—Keil & Weinkauf

[57] ABSTRACT

Novel triazoloquinazolines of the formula I

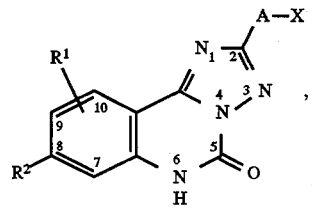

where A, X R¹ and R² have the meanings stated in the description, and their preparation are described. The compounds are suitable for controlling diseases.

3 Claims, No Drawings

TRIAZOLOQUINAZOLINES, THEIR PREPARATION AND USE

The present invention relates to novel triazoloquinazolines, to a process for their preparation and to their use for controlling diseases.

Pyrazolo- and triazoloquinazolines having antiallergic and antiinflammatory properties have been disclosed (EP 80,176, U.S. Pat. Nos. 4,053,600, 4,128,644). Pyrazoloquinazolines which are additionally suitable for treating thrombosis and neurological disorders have also been disclosed (U.S. Pat. No. 5,153,196).

We have now found that triazoloquinaolines of the formula I

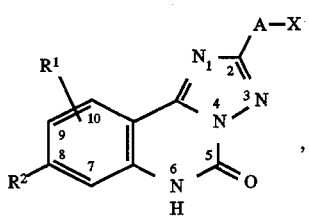

where

A is $C_{1-5}$-alkylene,

X is carboxyl which can be in the form of its salt with a physiologically tolerated amine cation or metal cation; the radical

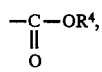

where $R^4$ is $C_{1-8}$-alkyl, cycloalkyl with 3 to 8 carbon atoms in the ring, benzyl, one of the radicals —$(CH_2)_n$—O—$R^5$ or

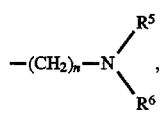

where n is the number 2, 3 or 4 and $R^5$ and $R^6$ are each $C_{1-3}$-alkyl; hydroxyl, $C_{1-4}$-hydroxyalkyl, $C_{1-4}$-alkylcarbonyl, nitrile O—$C_{1-4}$-alkyl, tetrazolyl, carbonylaminotetrazole or unsubstituted or substituted carbamoyl, and $R^1$ and $R^2$, which can be identical or different, are each hydrogen, fluorine, chlorine or bromine, trifluoromethyl, cyano, nitro, amino, $C_{1-5}$-alkyl, mono- or di-$C_{1-5}$-alkylamino, $C_{1-6}$-alkylthio, $C_{1-6}$-alkylsulfenyl, $C_{1-6}$-alkylsulfonyl, aminosulfonyl, di-$C_{1-6}$-alkylaminosulfonyl, or $R^1$ and $R^2$ together are methylene- or ethylenedioxy or straight-chain $C_{3-5}$-alkylene, or an aromatic or heterocyclic ring, show a different spectrum of effects.

Preferred compounds of the formula I are those where A and X have the stated meanings, and $R^1$ is hydrogen or chlorine or trifluoromethyl, nitro or $C_{1-3}$-alkyl, and $R^2$ is chlorine or trifluoromethyl, nitro or $C_{1-3}$-alkyl, or $R^1$ and $R^2$ together are straight-chain $C_{3-5}$-alkylene or an aromatic ring.

The following examples may be mentioned of radicals A—X in position 2 of the abovementioned 1,2,4-triazolo[1,5-c]quinazolin-5-ones:

acetyl, 2-propionyl, 3-propionyl, 4-butyryl, 3-butyryl, 2-butyryl, 5-valeryl, 4-valeryl, 3-valeryl and their methyl, ethyl, propyl, isopropyl, butyl, pentyl, hexyl, heptyl, cyclopropyl, cyclobutyl, cyclopentyl, cyclohexyl, cycloheptyl and cyclooctyl esters in each case or their amides such as methylamides, dimethylamides, ethylamides, diethylamides, propylamides, butylamides and benzylamides;

hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, hydroxypentyl, hydroxyheptyl;

methoxymethyl, 1-methoxypropyl, 2-methoxypropyl, 3-methoxypropyl, methoxybutyl, ethoxymethyl, 1-ethoxypropyl, 2-ethoxypropyl, 3-ethoxypropyl, ethoxybutyl, oxomethyl, 1-oxoethyl, 2-oxoethyl, 1-oxopropyl, 2-oxopropyl, 3-oxopropyl, 1-oxobutyl, 2-oxobutyl, 3-oxobutyl, 4-oxobutyl, 1-oxopentyl, 2-oxopentyl, 3-oxopentyl, 4-oxopentyl, cyanomethyl, 1-cyanoethyl, 1-cyanopropyl, 2-cyanopropyl, 3-cyanopropyl, 1-cyanobutyl, 2-cyanobutyl, 3-cyanobutyl, 4-cyanobutyl.

The following may be mentioned as basic structure without the substituents AX:

10-Chloro-1,2,4-triazolo[1,5-c]quinazolin-5-one
8-Chloro-1,2,4-triazolo[1,5-c]quinazolin-5-one
7-Chloro-1,2,4-triazolo[1,5-c]quinazolin-5-one
8,10-Dichloro-1,2,4-triazolo[1,5-c]quinazolin-5-one
10-Bromo-1,2,4-triazolo[1,5-c]quinazolin-5-one
9-Bromo-1,2,4-triazolo[1,5-c]quinazolin-5-one
8-Bromo-1,2,4-triazolo[1,5-c]quinazolin-5-one
7-Bromo-1,2,4-triazolo[1,5-c]quinazolin-5-one
8,10-Dibromo-1,2,4-triazolo[1,5-c]quinazolin-5-one
10-Iodo-1,2,4-triazolo[1,5-c]quinazolin-5-one
9-Iodo-1,2,4-triazolo[1,5-c]quinazolin-5-one
8-Iodo-1,2,4-triazolo[1,5-c]quinazolin-5-one
7-Iodo-1,2,4-triazolo[1,5-c]quinazolin-5-one
8,10-Diiodo-1,2,4-triazolo[1,5-c]quinazolin-5-one
10-Iodo-8-chloro-1,2,4-triazolo[1,5-c]quinazolin-5-one
9-Trifluoromethyl-1,2,4-triazolo[1,5-c]quinazolin-5-one
9-Trifluoromethyl-8-nitro-1,2,4-triazolo[1,5-c]quinazolin-5-one
9-Trifluoromethyl-8-methanesulfonyl-1,2,4-triazolo[1,5-c]quinazolin-5-one
9-Methyl-8-nitro-1,2,4-triazolo[1,5-c]quinazolin-5-one
9-Ethyl-8-nitro-1,2,4-triazolo[1,5-c]quinazolin-5-one
9-Cyano-8-nitro-1,2,4-triazolo[1,5-c]quinazolin-5-one
10-Cyano-1,2,4-triazolo[1,5-c]quinazolin-5-one
9-Cyano-1,2,4-triazolo[1,5-c]quinazolin-5-one
8-Cyano-1,2,4-triazolo[1,5-c]quinazolin-5-one
7-Cyano-1,2,4-triazolo[1,5-c]quinazolin-5-one
9-Cyano-8-methanesulfonyl-1,2,4-triazolo[1,5-c]quinazolin-5-one
9-Cyano-8-trifluoromethyl-1,2,4-triazolo[1,5-c]quinazolin-5-one
10-Methyl-1,2,4-triazolo[1,5-c]quinazolin-5-one
8-Methyl-1,2,4-triazolo[1,5-c]quinazolin-5-one
7-Methyl-1,2,4-triazolo[1,5-c]quinazolin-5-one
9-Methyl-1,2,4-triazolo[1,5-c]quinazolin-5-one
9,10-Dimethyl-1,2,4-triazolo[1,5-c]quinazolin-5-one
7,8-Dimethyl-1,2,4-triazolo[1,5-c]quinazolin-5-one
9,10-Tetramethylene-1,2,4-triazolo[1,5-c]quinazolin-5-one
7,8-Tetramethylene-1,2,4-triazolo[1,5-c]quinazolin-5-one
9,10-Trimethylene-1,2,4-triazolo[1,5-c]quinazolin-5-one
8,9-Trimethylene-1,2,4-triazolo[1,5-c]quinazolin-5-one
7,8-Trimethylene-1,2,4-triazolo[1,5-c]quinazolin-5-one
9,10-Pentamethylene-1,2,4-triazolo[1,5-c]quinazolin-5-one
8,9-Pentamethylene-1,2,4-triazolo[1,5-c]quinazolin-5-one 7,8-Pentamethylene-1,2,4-triazolo[1,5-c]quinazolin-5-one 10-Isopropyl-1,2,4-triazolo[1,5-c]quinazolin-5-one
9-Isopropyl-1,2,4-triazolo[1,5-c]quinazolin-5-one
8-Isopropyl-1,2,4-triazolo[1,5-c]quinazolin-5-one
7-Isopropyl-1,2,4-triazolo[1,5-c]quinazolin-5-one
9,10-Benzo-1,2,4-triazolo[1,5-c]quinazolin-5-one
8-Sulfonylamido-1,2,4-triazolo[1,5-c]quinazolin-5-one
8-Sulfonylamido-9-trifluoromethyl-1,2,4-triazolo[1,5-c]quinazolin-5-one
10-Methylthio-1,2,4-triazolo[1,5-c]quinazolin-5-one
9-Methylthio-1,2,4-triazolo[1,5-c]quinazolin-5-one
8-Methylthio-1,2,4-triazolo[1,5-c]quinazolin-5-one
7-Methylthio-1,2,4-triazolo[1,5-c]quinazolin-5-one
9-Methylthio-8-nitro-1,2,4-triazolo[1,5-c]quinazolin-5-one 8-Trifluoromethanesulfonyl-1,2,4-triazolo[1,5-c]quinazolin-5-one
9-Trifluoromethanesulfonyl-8-nitro-1,2,4-triazolo[1,5-c]quinazolin-5-one 10-Dimethylamino-1,2,4-triazolo[1,5-c]quinazolin-5-one
9-Dimethylamino-1,2,4-triazolo[1,5-c]quinazolin-5-one
8-Dimethylamino-1,2,4-triazolo[1,5-c]quinazolin-5-one
8,9-Methylenedioxy-1,2,4-triazolo[1,5-c]quinazolin-5-one
9,10-Methylenedioxy-1,2,4-triazolo[1,5-c]quinazolin-5-one
9-Butoxy-1,2,4-triazolo[1,5-c]quinazolin-5-one
8-Butoxy-9-cyano-1,2,4-triazolo[1,5c]quinazolin-5-one The compounds of the formula I are prepared by intramolecular condensation of a hydrazinoquinazoline of the formula II

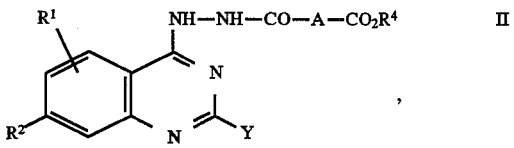

where A, $R^1$ and $R^2$ have the meanings stated for formula I, $R^4$ is $C_{1-8}$-alkyl, cycloalkyl with 3 to 8 carbon atoms in the ring, a benzyl ring or the radical —$(CH_2)$—$OR^5$, and Y is hydroxyl or bromine or chlorine, preferably in the presence of a dehydrating agent, in particular of phosphorus oxychloride, polyphosphoric acid or acetic acid, with or without an inert solvent such as toluene, chlorobenzene, xylene or excess acetic acid, at from 50° to 150° C., preferably at the reflux temperature of the reaction mixture.

The esters obtained in this way can subsequently be hydrolyzed, and the free acids can be converted into physiologically tolerated salts with an amine or a metal cation. The free acids can also be reduced to the hydroxyalkyl compounds (A—X=hydroxyalkyl) or converted by conventional methods into the nitriles, tetrazolemino and carbamoyl compounds.

The esters of the formula I can also be subjected to a conventional transesterification process appropriate for the meanings of the radical $R^4$.

The compounds of the formula I where X is carboxyl are prepared by hydrolysis of the corresponding esters, preferably under alkaline conditions, for example in the presence of an alkali metal hydroxide or of sodium bicarbonate, in a solvent such as water, a lower alcohol, tetrahydrofuran or mixtures thereof. The organic acids obtained in this way are converted where appropriate into a physiologically tolerated amine or metal salt. This means, in particular, salts of the alkali metals such as sodium and potassium, of the alkaline earth metals such as calcium, of other metals such as aluminum, and salts of organic bases such as morpholine, piperidine, mono-, di- and triethanolamine or tris (hydroxymethyl)aminomethane, which are generally known to the skilled worker.

Carboxylic acids of the formula I can furthermore be prepared by hydrogenolysis of the corresponding benzyl esters by conventional methods as described, for example, in Houben-Weyl, Vol. IV/1c, pages 381 et seq. The reaction takes place in the presence of a catalyst such as platinum, palladium or nickel, expediently on a support, in particular carbon, in a solvent such as a lower alcohol, especially methanol, acetic acid or a dialkylformamide, in particular dimethylformamide, at from 0° C. to the boiling point of the solvent, and preferably under only slightly elevated pressure.

Amides of the formula I where X is carbamoyl, are obtained by reacting the esters with ammonia or amines in the presence of a solvent such as water, a lower alcohol, an aqueous alcoholic solution or dialkylformamide at from 0° C. to the reflux temperature of the system.

Treatment of primary amides with a dehydrating agent such as phosphorus pentoxide, phosphorus oxychloride or thionyl chloride results in the nitriles of the compounds of the formula I where X is a nitrile group. The reaction is generally carried out with an excess of dehydrating agent at the reflux temperature of the mixture. It is possible where appropriate to carry out the reaction in the presence of an inert solvent such as benzene or ethylene chloride.

The compounds of the formula I where X is a tetrazole radical are synthesized by conventional methods as described, for example, in Synth. 1973, 80, by reacting the amides with hydrazoic acid or one of its salts, for example with alkali metal or alkaline earth metal azides, in the presence or absence of Lewis acids such as aluminum chloride and tin chloride or of ammonium chloride. The combination of sodium azide with chloride is preferred. The reaction is generally carried out in the presence of an inert solvent such as benzene, tetrahydrofuran or dimethylformamide at from room temperature to 150° C. The tetrazolyl compounds are highly acidic and can be converted in a conventional way into a salt with a physiologically tolerated amine cation or metal cation.

Reduction of carboxylic acids, in particular of an ester of a compound of the formula I, by conventional processes, for example using a complex metal hydride such as lithium borohydride, in the presence of an ether such as tetrahydrofuran as solvent provides the hydroxymethyl compounds of the formula I (X=$CH_2OH$). The reduction is preferably carried out at the boiling point of the reaction mixture.

Compounds of the formula I with a carbonylaminotetrazole radical for X (X=CO—NH—$CHN_4$) can be obtained by conventional methods by condensation of the basic carboxylic acid with 5-aminotetrazole of the formula III

The reaction is usually carried out in an inert solvent such as, for example, methylene chloride, dioxane, tetrahydrofuran or dimethylformamide, preferably in the presence of a condensing reagent known from peptide chemistry, such as N,N'-carbonyldiimidazole or N,N'-dicyclohexylcarbodiimide, at from 20° C. to 120° C.

Compounds of the formula I where X is an unsubstituted or substituted carbamoyl radical can also be prepared in a similar way from the corresponding acids.

If the substituents $R^1$ and $R^2$ are not yet present in the starting compounds, they can also be introduced subsequently. This can take place by an electrophilic aromatic substitution of a resulting compound of the formula I where $R^1$ and/or $R^2$ are hydrogen by conventional methods as described, for example, in Houben-Weyl, Vol. X/1, pages 471 et seq., Vol. IX, pages 572 et seq. and Vol. V/3, page 873. Thus, the nitration can be carried out with a mixture of sulfuric and nitric acids at room temperature, the sulfonation can be carried out, for example, with chlorosulfonic acid at from room temperature to 150° C., and the chlorination can be carried out with sulfuryl chloride at from 20° C. to 100° C.

The starting compounds of the formula II are prepared in a conventional way by condensing a hydrazinoquinazoline of the formula IV

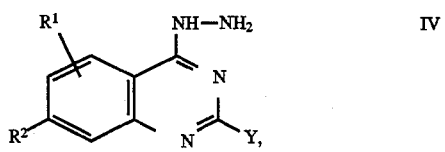

where $R^1$, $R^2$ and Y have the abovementioned meanings, with a dicarboxylic ester halide or a dicarboxylic diester. When an ester halide, preferably a chloride, is used, the reaction expediently takes place at from −30° C. to 70° C., preferably at room temperature, in an inert solvent such as dimethylformamide, dioxane, tetrahydrofuran or methylene chloride. The reaction is preferably carried out in the presence of tertiary organic bases such as triethylamine or pyridine.

The reaction of IV with esters can be carried out with or without solvents such as toluene, chlorobenzene or diphenyl ether, at from about 20° C. to the reflux temperature of the mixture.

Another process for preparing starting compounds of the formula II comprises reacting an acylhydrazine of the formula V

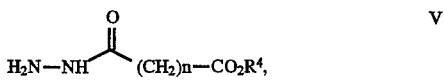

where $R^4$ has the abovementioned meaning, with a quinazoline of the formula VI

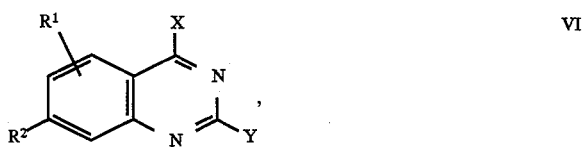

where $R^1$, $R^2$ and Y have the abovementioned meanings, and X is a nucleofugic leaving group, preferably a halogen atom, such as chlorine. The reaction is carried out at from 0° C. to 50° C. in an inert solvent such as ethanol, methylene chloride, toluene, tetrahydrofuran or dimethylformamide, preferably with an excess of V.

Synthesis of compounds of the formulae IV and VI is described in EP 80 176.

The compounds I according to the invention are suitable as pharmaceutical agents for human and veterinary medicine and can be used to produce drugs for the treatment of neurodegenerative disorders and neurotoxic disturbances of the central nervous system and for producing spasmolytics, antiepileptics, anxiolytics and antidepressants.

The pharmacological activity of the compounds I according to the invention was investigated on isolated membrane material from rat cerebra. To do this, the membrane material was treated in the presence of the compounds according to the invention with the radiolabeled substances $^3$H-2-amino-3-hydroxy-5-methyl-4-isoxazolepropionic acid ($^3$H-AMPA) and $^3$H-2-amino-3-hydroxy-5-methyl-4-isoxazolepropionic acid ($^3$H-AMPA) and $^3$H-5,7-dichlorokynurenic acid, the latter binding to specific receptors (AMPA receptor and NMDA receptor (N-methyl-D-aspartate) respectively). The radioactivity of the treated membranes was subsequently measured by scintillation counting. The amounts of bound $^3$H-AMPA and $^3$H-5,7-dichlorokynurenic acid, or in each case the amounts of these radiolabeled substances displaced, were determined from the bound radioactivity. The dissociation constant $K_I$ (I=inhibitor) resulting from this, which is a measure of the displacing effect of the agent according to the invention, was found by iterative nonlinear regression analysis using the Statistical Analysis System (SAS) on an IBM computer, similar to the Ligand program of P. J. Munson or D. Rodbard (Analytical Biochem. 107, 220 (1980), Ligand: Versatile Computerized Approach for Characterization of Ligand Binding Systems).

The following in vitro investigations were carried out:
1. Binding of $^3$H-2-amino-3-hydroxy-5-methyl-4-isoxanolpropionic acid ($^3$H-AMPA)

To prepare the membranes, freshly removed rat cerebra were homogenized together with about 15 times the volume of a buffer solution A composed of 30 mM α,α,α-tris (hydroxymethyl)methylamine hydrochloride (TRIS-HCl) and 0.5 mM ethylenediaminetetraacetic acid (EDTA), pH 7.4, using an Ultra-TURRAX. The suspension was centrifuged at 48,000 g for 20 min. After removal of the supernatant liquid, the proteinaceous membrane material present in the sediment was washed three times by suspension in buffer solution A and subsequent centrifugation at 48,000 g for 20 minutes each time. The membrane material was then suspended in 15 times the volume of buffer solution A and incubated at 37° C. for 30 minutes. The protein material was subsequently washed twice by centrifugation and suspension and stored at −70° C. until used.

For the binding assay, the protein material was thawed at 37° C. and washed twice by centrifugation at 48,000 g (20 minutes) followed by suspension in a buffer solution B composed of 50 mM TRIS-HCl, 0.1 M potassium thiocyanate and 2.5 mM calcium chloride, pH 7.1. Subsequently 0.25 mg of membrane material, 0.1 µCi of $^3$H-AMPA (60 Ci/mmol) and compound I were dissolved in 1 ml of buffer solution B and incubated on ice for 60 minutes. The incubated solution was filtered through a CF/B filter (from Whathman) which had previously been treated with a 0.5% strength aqueous solution of polyethyleneimine for at least 2 hours. The filtrate [sic] was then washed with 5 ml of cold buffer solution B in order to separate bound and free $^3$H-AMPA from one another. After the radioactivity of the bound $^3$H-AMPA in the membrane material had been measured by scintillation counting, the $K_I$ was determined by subjecting the displacement plots to regression analysis.

The following results were obtained:

| Example No. | AMPA binding Ki [µM] |
| --- | --- |
| 13 | 3.4 |
| 14 | 0.6 |
| 15 | 1.0 |
| 18 | 0.6 |
| 19 | 0.7 |
| 20 | 0.6 |

2. Binding of $^3$H-5,7-dichlorokynurenic acid

To prepare the membrane material, freshly removed rat cerebra were homogenized together with about 10 times the volume of a buffer solution A' composed of 50 mM TRIS- HCl and 10 mM EDTA, pH 7.4. The suspension was centrifuged at 48,000 g for 20 minutes. After removal of the supernatant liquid, the membrane material present in the sediment was washed twice by suspension in buffer solution A' and subsequent centrifugation for 20 minutes each time and suspension. After resuspension of the membranes in buffer solution A' and freezing in liquid nitrogen, the suspension was thawed again at 37° C. and, after another wash step, incubated at 37° C. for 15 minutes. The protein material was subsequently washed by centrifugation and suspension four times and was stored at −70° C. until used.

For the binding assay, the protein material was thawed at 37° C. and washed twice by centrifugation at 48,000 g (20 minutes) followed by suspension in a buffer solution B' composed of 50 mM TRIS-HCl, pH 7.4. Subsequently 0.15 mg of membrane material, 0.3 µCi of $^3$H-5,7-dichlorokynurenic acid (16 Ci/mmol) and compound I were dissolved in 1 ml of buffer solution B' and incubated on ice for 30 minutes. The incubated solution was centrifuged at 150,000 g for 2 minutes. After removal of the supernatant liquid, the sediments were suspended twice in 1.5 ml of cold buffer solution B' each time. After the radioactivity of the $^3$H-5,7-dichlorokynurenic acid bound to the membranes in the sediment had been measured, the $K_I$ was found by subjecting the displacement plots to regression analysis.

The following results were obtained:

| Example No. | Binding of dichloro-kynurenic acid Ki [µM] |
|---|---|
| 4 | 1.75 |
| 13 | 0.5 |
| 14 | 0.17 |
| 15 | 0.4 |
| 16 | 0.1 |
| 18 | 0.65 |
| 19 | 0.3 |
| 20 | 0.4 |
| 21 | 0.8 |

The drug preparations are produced in a conventional way, eg. by mixing the agent with the other conventional excipients and diluents.

The drug preparations can be administered in various ways such as orally, parenterally, subcutaneously, intraperitonally [sic] and topically. Thus, possible formulations are as tablets, emulsions, solutions for infusion and injection, pastes, ointments, gels, creams, lotions, dusting powders and sprays.

The drug preparations according to the invention contain a therapeutically effective amount of the compound I in addition to conventional pharmaceutical ancillary substances. The agents can be present in the conventional concentrations for local external use, eg. in dusting powders and ointments. As a rule, the agents are present in an amount of from 0.001 to 5% by weight, preferably 0.02 to 0.5% by weight.

On internal use, the preparations are administered in single doses. From 0.1 to 50 mg, preferably 0.1 to 10 mg, of agent are given per kg of body weight in a single dose. The preparations can be administered in one or more dosages each day depending on the nature and severity of the disorders. The daily dose is usually from 0.1 to 100 mg per kg of body weight on oral administration and from 0.01 to 10 mg per kg of body weight on parenteral administration.

The pharmaceutical preparations according to the invention contain, besides the agent, the conventional excipients and diluents appropriate for the desired mode of administration. For local external administration it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable examples for internal administration are lactose, propylene glycol, ethanol, starch, talc and polyvinylpyrrolidone.

It is furthermore possible for antioxidants such as tocopherol and butylated hydroxyanisole, as well as butylated hydroxytoluene, flavor-improving additives, stabilizers, emulsifiers and bleaches to be present.

The substances present in the preparation in addition to the agent, as well as the substances used in the production of the pharmaceutical preparation must be toxicologically acceptable and compatible with the agent in each case.

The following examples illustrate the invention in detail.

A. PREPARATION OF STARTING COMPOUNDS

EXAMPLE a

2-Chloro-4-N(N'-ethylsuccinylhydrazino)quinazoline 3 g of 2-chloro-4-hydrazinoquinazoline were suspended in 100 ml of methylene chloride and 2 ml of triethylamine and, at 0° C., 3 g of ethyl succinyl chloride were added dropwise. The mixture was stirred at room temperature overnight, and the precipitate was filtered with suction, washed with water and dried. Yield: 4.1 g (82%).

The following were prepared similarly from the appropriate hydrazinoquinazolines and ester chlorides:

2-Chloro-4-N(N'-ethylglutarylhydrazino)quinazoline

2-Chloro-4-N(N'-ethylmalonylhydrazino)-9-nitroquinazoline

2-Chloro-8,9-dimethyl-4-N(N'-ethylsuccinylhydrazino)quinazoline

B. PREPARATION OF THE FINAL PRODUCTS

EXAMPLE 1

Ethyl 3-(1,2,4-triazolo[1,5-c]quinazolin-5-on-2) propionate 32 g of 2-chloro-4-N(N'-ethylsuccinylhydrazino) quinazoline were refluxed in 500 ml of acetic acid for 2 h. The solvent was removed by distillation, and the residue was treated with methanol, filtered off with suction and dried. Yield: 19.4 g (68%); m.p. 208°–210° C.

The following compounds were prepared in a similar way starting from the appropriate compounds:

2. Methyl 4-(1,2,4-triazolo[1,5-c]quinazolin-5-on-2)-butyrate, m.p. 176°–179° C.

3. Ethyl 2-(1,2,4-triazolo[1,5-c]quinazolin-5-on-2)-acetate, m.p. 206°–210° C.

4. Methyl 3-(8,9-dimethyl-1,2,4-triazolo[1,5-c] quinazolin-5-on-2)propionate, m.p. 253°–258° C.

5. Ethyl 3-(8-trifluoromethyl-1,2,4-triazolo[1,5-c]-quinazolin-5-on-2)propionate, m.p. 220°–222° C.

EXAMPLE 6

4-(1,2,4-Triazolo[1,5-c]quinazolin-5-on-2)butyric acid 3.5 g of substance from Example 2 were stirred in 70 ml of 1 N sodium hydroxide solution at room temperature overnight. The solution was extracted with $CH_2Cl_2$, the aqueous phase was adjusted to pH 1 with 1 N hydrochloric acid, and the precipitate was filtered off with suction, washed with water and dried. Yield: 2.8 g (84%); m.p. 266°–270° C.

The following compounds were prepared in a similar way:

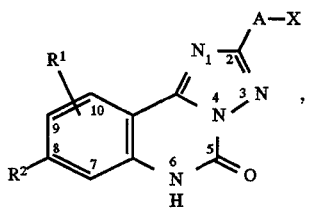

| Ex. | R¹ | R² | n | M.p. [C.] |
|---|---|---|---|---|
| 7 | H | H | 2 | 315–317 |
| 8 | 9-NO₂ | H | 2 | 250–254 |
| 9 | 9-NO₂ | H | 3 | 153–157 |
| 10 | H | H | 1 | 330–335 |
| 11 | 9-NO₂ | H | 1 | 315–320 |
| 12 | 9-Cl | H | 2 | 300–301 |
| 13 | 8-NO₂ | H | 3 | 234–236 |
| 14 | 8-NO₂ | H | 2 | 272–273 |
| 15 | 8-NO₂ | 9-NO₂ | 2 | 224–226 |
| 16 | 8-CH₃ | 9-CH₃ | 2 | >350 |
| 17 | 8-CF₃ | 9-NO₂ | 2 | 241–243 |
| 18 | 8-CF₃ | H | 2 | 293–295 |
| 19 | 7,8-benzo | | 2 | 313–319 |
| 20 | 8,9-benzo | | 2 | 337–339 |

EXAMPLE 21

3-(8,9-Dimethyl-1,2,4-triazolo[1,5-c]quinazolin-5-on-2) propionic acid benzylamide 1.7 g of acid from Example 16 were stirred with 1.2 g of 1-hydroxybenzotriazole hydrate and 1.4 g of dicyclohexyl-carbodiimide in 15 ml of DMF for 90 min, and subsequently a solution of 0.65 g of benzylamine in 5 ml of DMF was added, and the mixture was stirred at room temperature for a further 15 h. The mixture was filtered, the filtrate was evaporated under reduced pressure, and the residue was washed with methylene chloride. Yield: 0.65 g (33%); m.p. 289°–294° C.

EXAMPLE 22

Ethyl 2-(9-nitro-1,2,4-triazolo[1,5-c]quinazolin-5-on-2) acetate 1 g of ester (Example 3) was stirred in a mixture of 10 g of concentrated sulfuric acid and 0.21 ml of concentrated nitric acid for 4 h. The mixture was poured into ice, and the precipitate was filtered off with suction, washed with water and dried. Yield: 0.75 g; m.p. 188°–190° C.

The following were prepared in a similar way,

23. Ethyl 3-(9-nitro-1,2,4-triazolo[1,5-c]quinazolin-5-on-2)propionate, m.p. 120°–126° C.

24. Methyl 4-(9-nitro-1,2,4-triazolo[1,5-c]quinazolin-5-on-2)butyrate, m.p. 192°–196° C.

EXAMPLE 25

Ethyl 3-(8-trifluoromethyl-9-nitro-1,2,4-triazolo{1,5-c]-quinazolin-5-on-2)propionate 5 g of ester (Example 5) were added in portions at 0° C. to a mixture of 10 ml of fuming nitric acid and 14.5 ml of concentrated sulfuric acid. After 2 h, the reaction mixture was poured into ice and extracted with ethyl acetate, the organic phase was dried and concentrated, and the residue was chromatographed on silica gel with methylene chloride/methanol (50:1). Yield: 2.0 g; m.p. 166°–168° C.

The following was prepared in a similar way:

EXAMPLE 26

Ethyl 3-(8,9-dinitro-1,2,4-triazolo[1,5-c]quinazolin-5-on-2)propionate, m.p. 170°–172° C.

We claim:

1. A triazoloquinazoline of the formula I

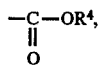

where

A is $C_1$–$C_5$-alkylene,

X is carboxyl which can be in the form of its salt with a physiologically tolerated amine cation or metal cation; the radical $$-\underset{\underset{O}{\|}}{C}-OR^4,$$

where $R^4$ is $C_1$–$C_8$-alkyl, and $R^1$ and $R^2$, which can be identical or different, are each hydrogen, fluorine, chlorine or bromine, trifluromethyl, nitro, $C_{1-5}$-alkyl, or $R^1$ and $R^2$ together are a benzo group.

2. A pharmaceutical composition for treating neurotoxic disturbances of the central nervous system comprising an effective amount of a compound of the formula I as defined in claim 1 and a pharmaceutically acceptable carrier therefor.

3. A method for treating neurotoxic disturbances of the central nervous system in mammals, which comprises administering to the mammalian host a pharmaceutically effective amount of a compound of the formula I as defined in claim 1.

* * * * *